(12) United States Patent
Krch, Sr. et al.

(10) Patent No.: US 8,694,083 B2
(45) Date of Patent: Apr. 8, 2014

(54) NOISE CANCELLATION MECHANISM

(75) Inventors: Russell W. Krch, Sr., Justice, IL (US);
Emil S. Golen, Barrington, IL (US);
Gregory A. Joseph, Naperville, IL (US)

(73) Assignee: Brunswick Corporation, Lake Forest, IL (US)

( * ) Notice: Subject to any disclaimer, the term of this patent is extended or adjusted under 35 U.S.C. 154(b) by 1183 days.

(21) Appl. No.: 12/152,936

(22) Filed: May 20, 2008

(65) Prior Publication Data

US 2009/0292216 A1  Nov. 26, 2009

(51) Int. Cl.
*A61B 5/00* (2006.01)

(52) U.S. Cl.
USPC .......................................... 600/520

(58) Field of Classification Search
USPC .......................................... 600/509, 519–521
See application file for complete search history.

(56) References Cited

U.S. PATENT DOCUMENTS

2002/0115938 A1* 8/2002 Hannula ........................ 600/509
2005/0197586 A1* 9/2005 Pearlman ...................... 600/509

* cited by examiner

*Primary Examiner* — Scott Getzow
(74) *Attorney, Agent, or Firm* — Michael E. McMurry

(57) ABSTRACT

In a biometric sensor provided for use with an exercise apparatus and having a pair electrodes for sensing a biopotential signal, a common-mode rejection circuit can be used to cancel noise in the signal resulting from various sources including motion of the apparatus.

20 Claims, 3 Drawing Sheets

NOISE CANCELLATION MECHANISM

FIELD

The present disclosure relates generally to exercise equipment and, more particularly, to a noise cancellation technique for biometric sensors associated with exercise equipment.

BACKGROUND

Heart rate monitors and other biometric sensors adapted for use with exercise equipment are becoming more prevalent. When the heart or other muscles contract, the body generates a very low amplitude electrical signal known as a biopotential signal. Biopotential signals can be electrically detected on the surface of a person's skin. Because the heart expands and contracts in a rhythmic manner, it generates a periodic biopotential signal which can be detected by a biometric sensor placed in contact with a person's skin.

Generally, heart rate monitors use electrodes to sense voltage fluctuations on a person's skin. The sensed signal is amplified and then filtered to identify the signal correlating to the heart rate. However, the use of high impedance, high gain amplifiers to measure differences in small electrical potentials can be complicated by unwanted electrical signals or noise if that noise is not present on both inputs to the amplifier. Since amplifiers do a good job of attenuating signals in common to both inputs, the difference does not contain the common noise. This is referred to as common-mode noise rejection.

A problem occurs when inputs to the amplifier senses voltage potentials that are physically separated from each other such that noise sources are picked up independently. In other words, the unwanted electrical signals are no longer common to the inputs of the amplifier. These non common-mode noise signals appear in the amplified signal and interfere with the signal of interest. This problem occurs in some types of exercise equipment. Therefore, it is desirable to provide a noise cancellation technique which may be employed with biometric sensors associated with such exercise equipment.

The statements in this section merely provide background information related to the present disclosure and may not constitute prior art.

SUMMARY

In the described apparatus a biometric sensor is provided that can be used with an exercise apparatus. In this example, the biometric sensor is comprised of: a first electrode disposed at a first location on the exercise apparatus for contact with a user and operable to receive a biopotential signal from the user; a second electrode disposed at a second location on the exercise apparatus for contact with the user and operable to receive a biopotential signal from the user, such that the first location is spatially separated from the second location; and an instrumentation amplifier is electrically coupled by a first wire to the first electrode and electrically coupled by a second wire to the second electrode, wherein the noise on the first electrode is proximally coupled to the second line and the noise on the second electrode is also proximally coupled to the first line, thereby creating a common-mode situation between inputs of the amplifier.

Further areas of applicability will become apparent from the description provided herein. It should be understood that the description and specific examples are intended for purposes of illustration only and are not intended to limit the scope of the present disclosure.

DRAWINGS

DETAILED DESCRIPTION

Figure 1:
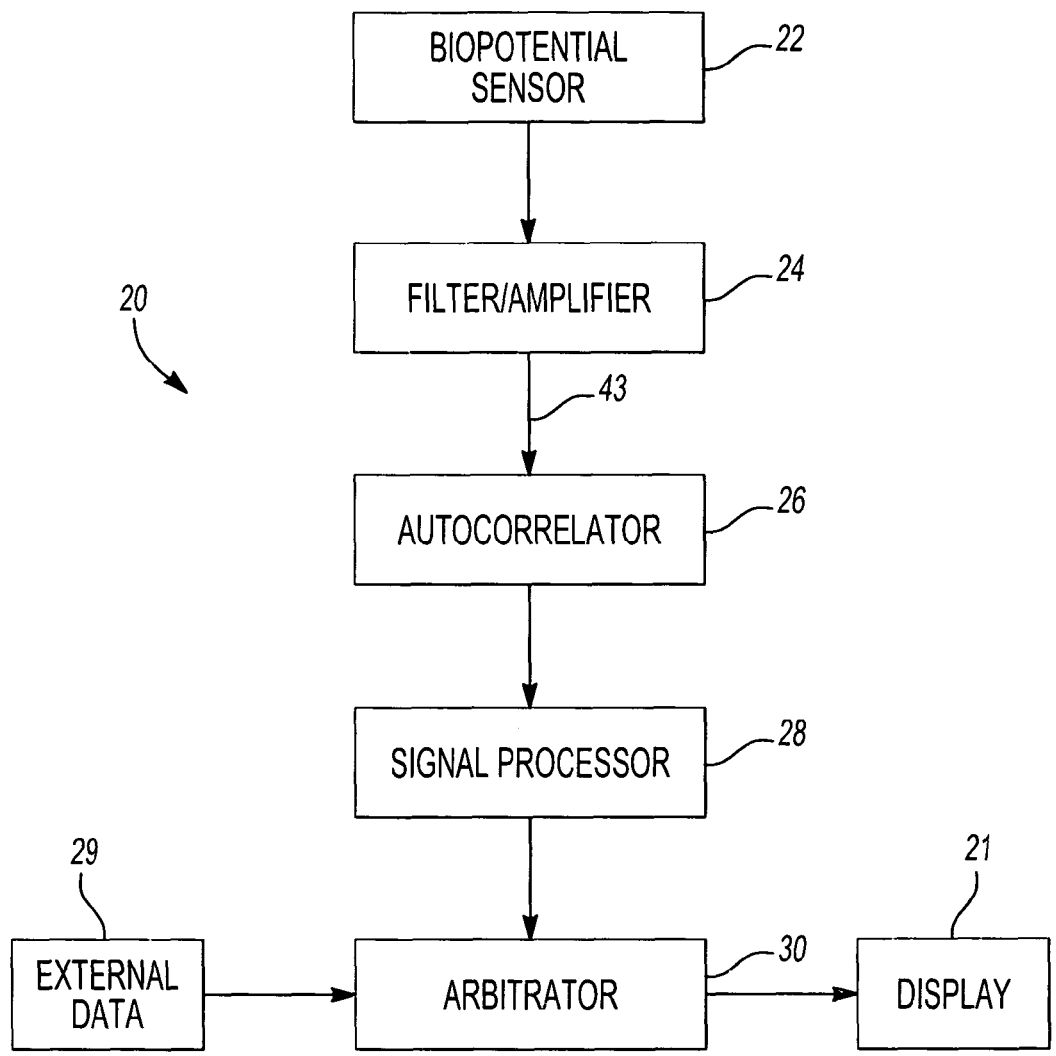
FIG. 1 is a block diagram of an exemplary heart rate monitor.

FIG. 1 is a block diagram for an exemplary heart rate monitor 20 that can form the environment for the described circuits. In this particular example, the heart rate monitor 20 includes a biopotential sensor 22, an amplifier-filter stage 24, an autocorrelator 26, a signal processor 28 and an arbitrator 30. When the biopotential sensor 22 is placed in contact with a person's skin, it captures an electrical signal corresponding to biopotential signals generated by the person. The human body produces biopotential signals when muscles, including the heart, expand and contract. Thus, the electrical signal captured by the biopotential sensor 22 includes signals corresponding to the person's heart beat from which a heart rate signal can be obtained. The electrical signal also includes noise and signals corresponding to other bodily functions.

In operation, the electrical signal is input to the amplifier-filter stage 24, where it is amplified and filtered. This output is then fed into the autocorrelator 26 that generates a signal, which represents autocorrelation of the output of the amplifier-filter stage 24. Autocorrelation algorithms are described in Pratical Approaches to Speech Coding, Panos E. Papamichalis, Prentice-Hall, Inc. Englewood Cliffs, N.J., 1987. The output of the autocorrelator 26 serves as input to the signal processor 28 that detects the presence of periodic signal in the output of the autocorrelator 26. The signal processor 28 generates a number of candidate signals, each of which corresponds to a heart rate measured in beats per minute. To generate these signals, signal processor 28 employs several signal indicators for detecting the presence of a signal that could correspond to a heartbeat. Each of these signal indicators employs a different technique and may generate one or more candidate signals.

The candidate signals are applied to the arbitrator 30, which uses predetermined criteria to decide which one of the candidate signals is most likely the subject's heart rate. The heart rate selected by arbitrator 30 may be displayed to the person on a monitor 21. The arbitrator 30 may take external data into account when selecting a heart rate. External data may also be supplied to the arbitrator 30 by an external data interface unit 29. The exact nature of the external data depends on the environment the heart rate monitor 20 is employed. For example, on an exercise device, the external data may be from a tachometer, an ergometer or other device designed to measure the amount of work performed by the person. Further details regarding this exemplary heart rate monitor may be found in U.S. Pat. No. 5,365,934 that is incorporated herein by reference. While the above description has been provided with reference to a particular heart rate monitor, it is readily understood that the broader aspects of this disclosure are applicable to other types of heart rate monitors and other biometric sensors.

Figure 2:
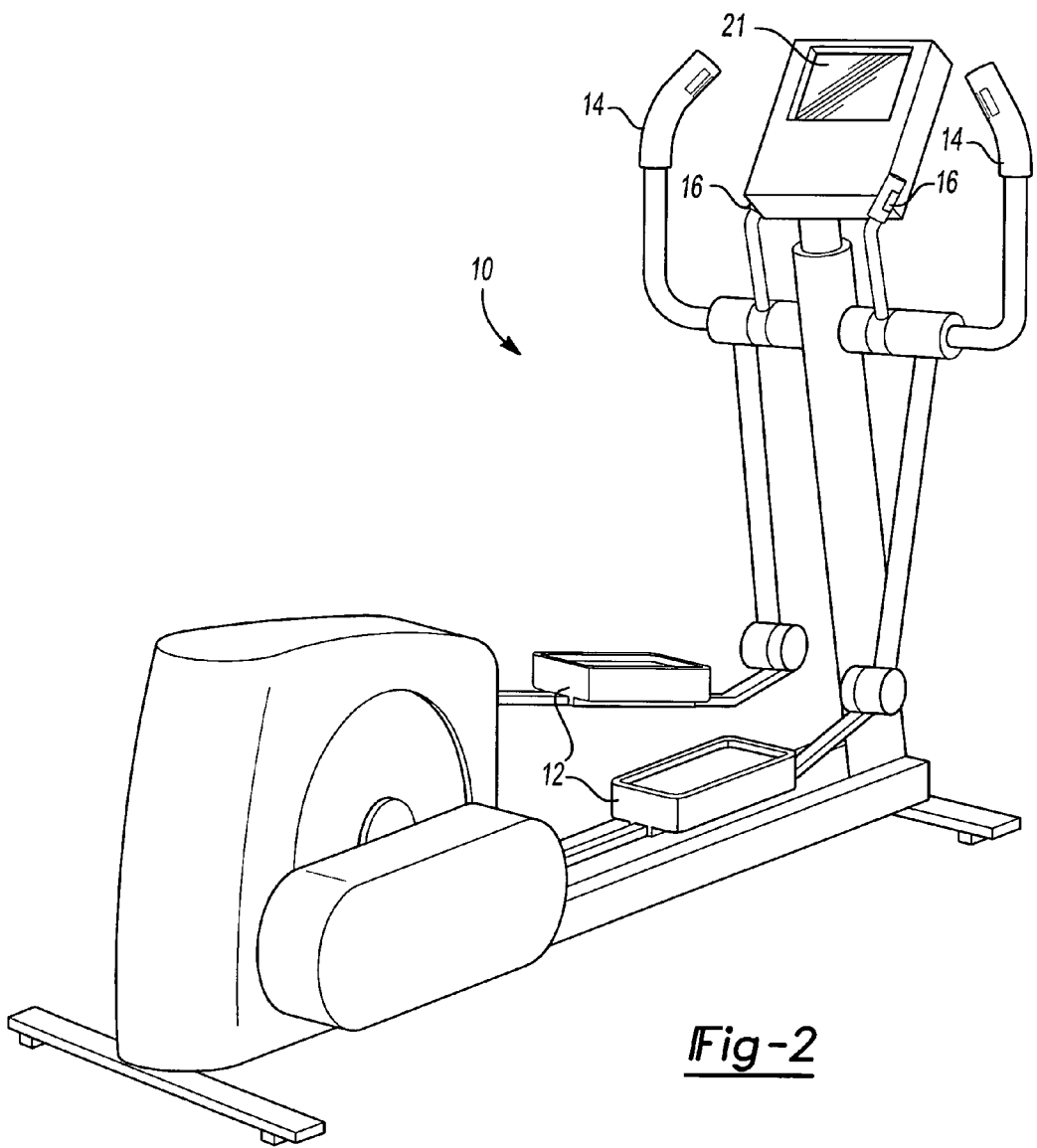
FIG. 2 is a diagram depicting an elliptical cross training device.

A heart rate monitor 20 may be integrated for use with a variety of exercise devices. For instance, the heart rate monitor 20 can be used with an elliptical cross training device 10 as shown in FIG. 2. Briefly, an elliptical cross trainer 10 is operated by a user standing on raised pedals 12 and holding handle bars positioned in front of the user. The trainer is preferably equipped with a movable pair of handle bars 14 and a stationary pair of handle bars 16. Users hold the handle bars while moving their feet along a path which forms an elliptical motion. In the case of the movable handle bars 14, the users can also push and pull the handle bars. In this way, the elliptical cross trainer 10 provides a low impact lower and upper body workout. An exemplary elliptical cross trainer is further described below. It is readily understood that the heart rate monitor may be integrated with other types of exercise equipment, such as a stationary bicycle, treadmill, etc. in the manner described below.

Figure 3:
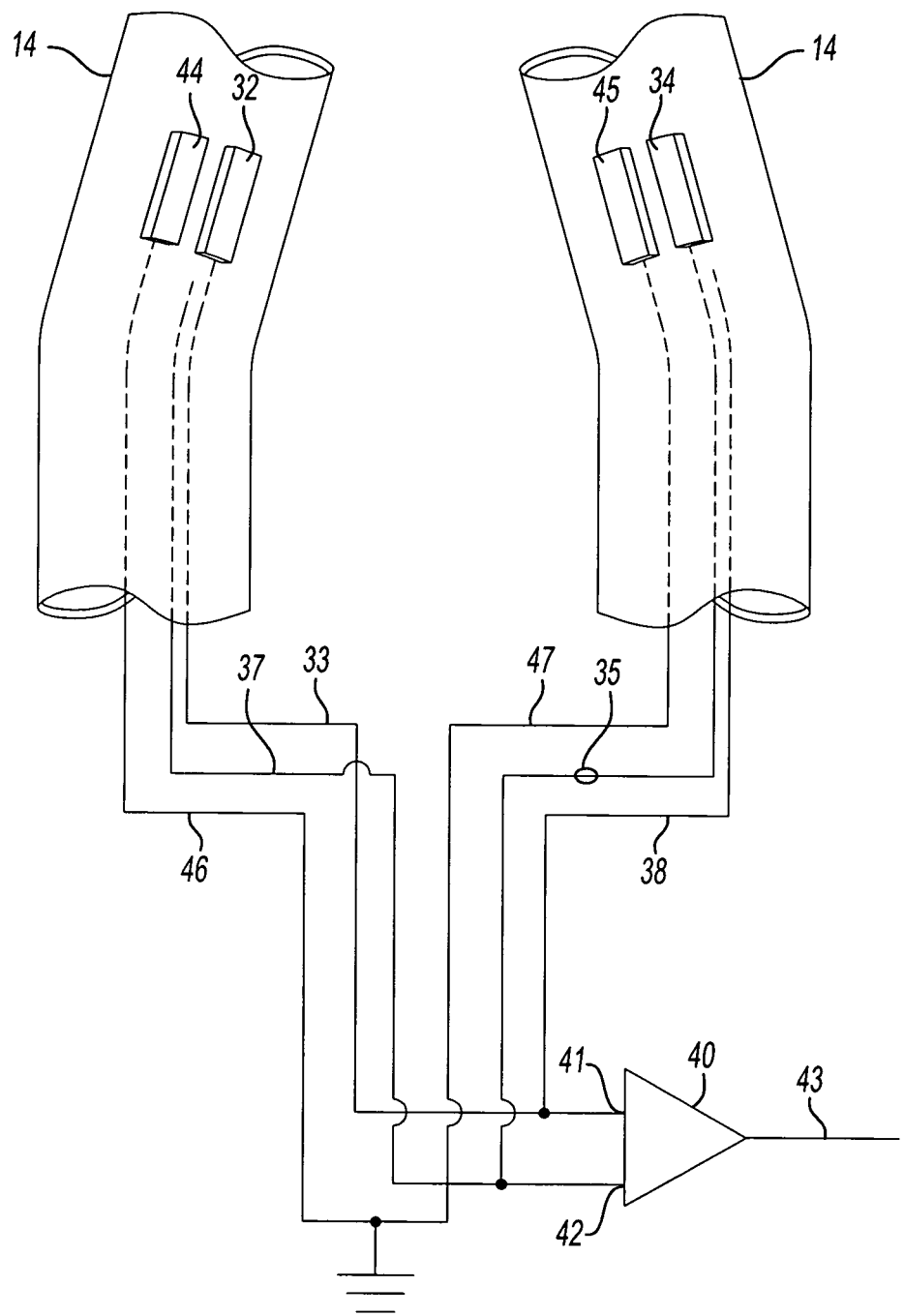
FIG. 3 is a schematic illustrating how an exemplary biometric sensor is integrated with an exercise device.

In the case of the elliptical cross trainer, the biopotential sensor 22 of the heart rate monitor 20 is integrated into at least one set of handle bars 14 as shown schematically in FIG. 3. The biopotential sensor 22 generally includes a pair of electrodes 32 and 34 disposed in each of the handle bars 14. Each of the electrodes 32 and 34 are electrically coupled via a wire 33 or 35 respectively to a first input 41 or a second input 42 of an instrumentation amplifier 40. In this example of a sensor arrangement, the electrodes 32, 34 are preferably rectangular-shaped strips of conductive material mounted on the handle bars 14 so their longitudinal edges are parallel with the longitudinal axis of the handle bars. A variety of other sensor arrangements can be used such as rings extending around the handles 14. In the arrangement of FIG. 3, the electrodes 32 and 34 are positioned along each handle bar 14 so that preferably it comes into direct physical contact with the palm of the user's hand when he grasps the handle bar 14. A similar arrangement can be employed for the other set of handle bars 16. Where it is desired that the user's skin is in contact with the electrodes during use of the exercise device, different positions and configurations for electrodes can be used.

Because in this case the electrodes 32 and 34 are located in each of the moving handles 14, a non common-mode noise can be created anywhere along the length of the wires 33 and 35. To create a balanced or forced common-mode situation, the noise source affecting the electrodes 32 and 34 or the wires 33 and 35 are further proximally connected to the other's input 41 or 42 of the amplifier 36. In this embodiment, the noise source on the electrode 32 or the wire 33 associated with the left side handle bar 14 is electrically coupled by a line 37 to the line 35 which extends from the electrode 34 on the right side handle bar 14. Likewise, the noise source on the electrode 34 or the wire 35 associated with the right side handle bar 14 is electrically coupled by a line 38 to the line 33 that extends from the electrode 32 on the left side handle bar 14. In addition, the secondary lines 37 and 38 are preferably connected to the other lines 33 and 35 in close proximity to the respective inputs 41 and 42 of the amplifier 40. This effectively removes the physical separation between the input signals and the amplifier 40. In this way, noise sources will affect both inputs in the same manner, thereby resulting in a common mode rejection. Accordingly, the signal at an output 43 of the amplifier 40 is more indicative of the signal of interest.

A pair of reference electrodes 44 and, 45 can also be disposed adjacent to each of the electrodes. The reference electrodes 44, 45 are in turn electrically coupled via lines 46, 47, respectively, to a ground (e.g., a metal frame of the exercise device). Other types of electrodes and/or arrangements for the electrodes are contemplated by this disclosure.

In some instances, the exercise apparatus may have multiple biopotential sensors associated with the heart monitor. Each sensor can include a pair of electrodes as described above. However, typically each electrode pair will be in a different location for grasping by the user during use of the exercise apparatus. In these cases, each electrode pair will preferably be electrically coupled to the same amplifier. An electrode pair that is not being grasped by the user effectively becomes an independent antenna susceptible in different ways to even the same noise source. Thus, by electrically and proximally coupling each electrode to both inputs of the amplifier, a common mode situation can also be created for this multiple sensor configuration.

It should also be appreciated that although the system as described above is designed to be used with biosensors such as 32 and 34 that are designed for direct physical contact with a user's skin, the principles of common mode rejection can be used with biosensors that are not in direct physical contact.

We claim:

1. A sensor for an exercise apparatus, comprising:
a first electrode disposed at a first location on the exercise apparatus for receiving a biopotential signal from a user;
a second electrode disposed at a second location on the exercise apparatus for receiving a biopotential signal from the user, the first location spatially separated from the second location;
an amplifier electrically having a first input coupled by a first line to the first electrode and having a second input electrically coupled by a second line to the second electrode; and
a common-mode circuit between said first and second inputs of the amplifier including a first circuit connected to said first input and proximally electrically coupled to said second line or said second electrode and a second circuit connected to said second input and proximally electrically coupled to said first line or said first electrode thereby creating a common-mode arrangement between inputs of the amplifier.

2. The sensor of claim 1 wherein said first circuit is connected to said first line in close proximity to said first input and said second circuit is connected to said second line in close proximity to said second input.

3. The sensor of claim 1 further comprises a reference electrode disposed adjacent to each of the first and second electrodes, where each reference electrode is electrically coupled to ground.

4. The sensor of claim 1 wherein the first and second electrodes are configured to make physical contact with the user during use of the exercise apparatus by the user.

5. The sensor of claim 1 wherein the first and second electrodes are configured to be grasped by a hand of the user.

6. The sensor of claim 1 wherein the first and second electrodes are disposed on handle bars of a cross training exercise device.

7. The sensor of claim 1 wherein the first and second electrodes are disposed on handle bars of a stationary bike.

8. An exercise apparatus, comprising:
a frame;
a pair of handles operatively coupled to the frame;
a biopotential sensor, having a first electrode integrated into one of said handles and a second electrode integrated into the other of said handles, for capturing a biopotential signal from a user of the exercise apparatus, the biopotential sensor further including an instrument amplifier, having a first input adapted to receive biopotential signals from a first of said electrodes and a second input adapted to receive biopotential signals from a second of said electrodes, operable to amplify the biopotential signals; and a common mode rejection circuit operatively associated with said first and second electrodes and connected to said first and second inputs.

9. The exercise apparatus of claim 8 wherein said common mode rejection circuit includes a pair of lines wherein each said line proximally electrically couples each of said electrodes to the opposite of said inputs of the amplifier.

10. The exercise apparatus of claim 8 having a first line connecting said first electrode to said first input of said amplifier and a second line connecting said second electrode connected to said second input of said amplifier and wherein said common mode rejection circuit includes a third line proximally electrically coupled with said first line and connected to said second input and a fourth line proximally electrically coupled with said second line and connected to said first input.

11. The exercise apparatus of claim 10 wherein said third line is additionally proximally electrically coupled with said first electrode and said fourth line is additionally proximally electrically coupled with said second electrode.

12. The exercise apparatus of claim 8 wherein the two electrodes of the biopotential sensor are configured to be grasped by a hand of the user.

13. The exercise apparatus of claim 8 wherein the two electrodes of the biopotential sensor are disposed on moveable handle bars of a cross training exercise device.

14. The exercise apparatus of claim 8 further comprises a second biopotential sensor having two electrodes disposed at a different location on the exercise apparatus, where the two electrodes from the second biopotential sensor are electrically coupled to each input of the amplifier.

15. A method for cancelling noise in a biopotential signal captured by a biometric sensor having two electrodes, comprising:
   capturing a first biopotential signal at a first electrode of the biometric sensor;
   transmitting via a first line said signal from said first electrode to a first input of an instrument amplifier;
   capturing a second biopotential signal at a second electrode, spatially separated from the first electrode, of the biometric sensor;
   transmitting via a second line said signal from said second electrode to a second input of an instrument amplifier; and
   utilizing a common mode rejection circuit including a pair of lines proximally electrically coupled to said first and second lines and said first and second electrodes and connected to said inputs to cancel noise in the biopotential signal.

16. The method of claim 15 wherein a first of said pair of lines is disposed to and proximally electrically coupled to said first line and connected to said second input of said instrument amplifier.

17. The method of claim 15 wherein a second of said pair of lines is disposed to and proximally electrically coupled to said second line and connected to said first input of said instrument amplifier.

18. The method of claim 15 wherein a first of said pair of lines is disposed to and proximally electrically coupled to said first electrode and connected to said second input of said instrument amplifier.

19. The method of claim 18 wherein a second of said pair of lines is disposed to and proximally electrically coupled to said second electrode and connected to said first input of said instrument amplifier.

20. The method of claim 19 wherein said first of said pair of lines is additionally disposed to and proximally electrically coupled to said first line and connected to said second input of said instrument amplifier and wherein said second of said pair of lines is additionally disposed to and proximally electrically coupled to said second line and connected to said first input of said instrument amplifier.

* * * * *